United States Patent [19]

Eiden et al.

[11] 4,002,617

[45] Jan. 11, 1977

[54] HYDRODIPYRANO-PHTHALAZINE COMPOUNDS

[75] Inventors: Fritz Eiden; Claus Schmiz, both of Munich, Germany

[73] Assignee: Chem. Pharmaz. Fabrik Dr. Herman Thiemann G.m.b.H., Lunen, Germany

[22] Filed: Nov. 5, 1975

[21] Appl. No.: 628,963

[30]     Foreign Application Priority Data

Nov. 4, 1974   Germany ........................ 2452491

[52] U.S. Cl. .................. 260/240 F; 260/250 P; 260/345.2; 424/250
[51] Int. Cl.$^2$ ..................... C07D 237/26
[58] Field of Search .............. 260/250 P, 240 F; 424/250

[56]       References Cited
           OTHER PUBLICATIONS

Knesebeck et al., Chem. Berichte 55, (1922), pp. 306–319.

*Primary Examiner*—Arthur P. Demers
*Attorney, Agent, or Firm*—Hugo E. Weisberger

[57]       ABSTRACT

The present invention relates to novel hydrodipyranophthalazine compounds of the formula:

wherein
 $R_1$ = hydrogen or lower alkyl,
 $R_2$ = hydrogen, chlorine or bromine,
 $R_3$ = hydrogen or aralkyl if $R_2$ = hydrogen,
 $R_3$ = bromine or alkoxy if $R_2$ = bromine,
 $R_3$ = chlorine or alkoxy if $R_2$ = chlorine, or wherein
 $R_4$ = hydrogen, halogen, trifluoromethyl, alkyl, alkoxyl, alkylenedioxy, a possibly substituted amino group, or a nitro group, the 4,4'-bond is saturated or unsaturated, and acid-addition salts of these compounds.

These compounds exert a valuable activity on the cardiovascular and central nervous system.

2 Claims, No Drawings

HYDRODIPYRANO-PHTHALAZINE COMPOUNDS

The invention relates to novel hydropyranophthalazine compounds, a process for the preparation thereof, and to pharmaceutical preparations containing such compounds as active ingredients.

More particularly, the invention relates to novel hydrodipyrano-phthalazine compounds of the structural formula:

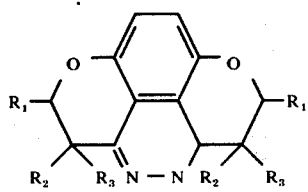

wherein
$R_1$ = hydrogen or lower alkyl,
$R_2$ = hydrogen, chlorine or bromine,
$R_3$ = hydrogen, chlorine, bromine, an alkoxy or aralkyl group, with the understanding that:
$R_3$ = hydrogen or aralkyl if $R_2$ = hydrogen,
$R_3$ = bromine or alkoxy if $R_2$ = bromine,
$R_3$ = chlorine or alkoxy if $R_2$ = chlorine, or
$R_2$ and $R_3$ form together the substituent

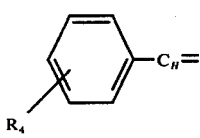

wherein
$R_4$ = hydrogen, halogen, trifluoromethyl, alkyl, alkoxyl, alkylenedioxy, a possibly substituted amino group, or a nitro group. the 4,4'-bond is saturated or unsaturated, and acid-addition salts of these compounds.

The compounds according to the invention possess very valuable biological properties and are particularly important in view of their activity on the cardiovascular and central nervous system. They exert antithrombose and antihistamine activity.

The present compounds can be prepared starting from 2,3,6,7-tetrahydro-benzo-[1,2-b, 4,3-b']4H,4H'-dipyrano-4,5-dione with the formula:

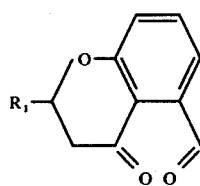

and reacting these compounds with hydrazine to obtain the compounds with the formula:

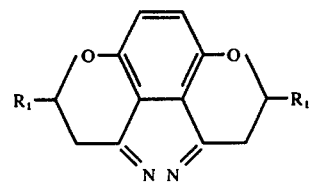

The substituents $R_2$ and $R_3$, possibly present in the positions 3 and 6 of the above compounds II may be introduced as follows:

These substituents being chlorine or bromine may be introduced by chlorination or bromination, preferably by treatment with chlorine or bromine in a suitable solvent like halogenated alkanes e.g. carbontetrafluoride, carbontetrachloride, chloroform or methylenechloride, or for the introduction of a chlorine substituent by treatment with $PCl_5$ in an aromatic hydrocarbon like benzene or toluene.

The thus obtained 3,3,6,6-tetra halo derivatives may be converted into 3,6-dihalo-3,6-dialkoxy compounds by treatment of the first mentioned compound with a metalalkoxide, e.g. sodiumalkoxide like sodiummethoxide.

The compounds with a benzylidene substituent in positions 3 and 6 may be obtained by reaction of a compound of the formula II with a benzaldehyde of the formula:

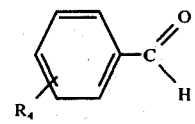

wherein $R_4$ has the meaning as defined above.

By reduction of the above compounds of the formula II, possibly substituted in 3- and 6-positions the 4,4'-unsaturated bond can be saturated. This reduction can be performed e.g. with an alkalimetal aluminium hydride, like lithium aluminium hydride.

The term "alkyl" in the substituents $R_1$ and $R_4$, and as a moiety in the substituents $R_3$ and $R_4$ means a lower alkyl group having 1–6 carbon atoms like methyl, ethyl, propyl, isopropyl, butyl, t-butyl, i-butyl, pentyl and hexyl, preferably methyl and ethyl.

The aralkyl group represented by substituents $R_3$ is preferably a benzyl or phenylethyl radical.

If the amino group represented by substituent $R_4$ is mono-, or di-substituted the substituent may be an alkyl or hydroxyalkyl radical. The substituted amino group is preferably the dimethylamino group.

The compound I to be used as starting products for the synthesis of the compounds according to the present invention may be prepared by the following route

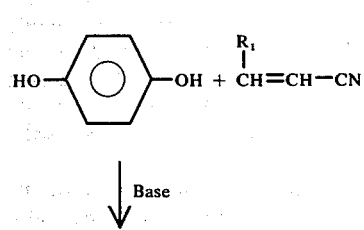

↓ Base

-continued

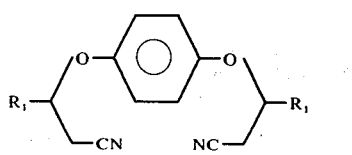

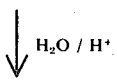

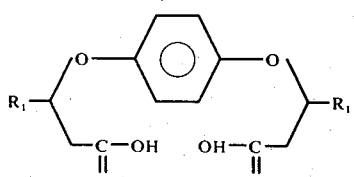

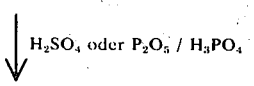

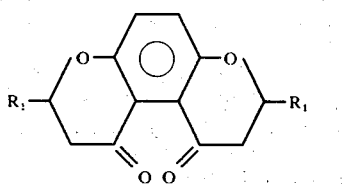

The compounds of the present invention can be administered parenterally, orally, sublingually, rectally or intranasally. For such administration the compounds are placed in a suitable form like tablets, dragees, capsules, emulsions, suspensions or solutions.

For oral administration a single dosage is preferably used from 10–150 mg, and a daily dosage from 30–500 mg.

For parenteral administration the single dosage is preferably between 5–100 mg, and the daily dosage between 50–300 mg.

Particularly for parental administration the compounds of formula II may be converted into acid addition salts thereof by reacting such a compound with a pharmaceutically acceptable organic or inorganic acid, such as hydrochloric acid, phosphoric acid, acetic acid, maleic acid, tartaric acid, citric acid, etc.

The invention is further illustrated by the following detailed examples.

PREPARATION OF STARTING PRODUCTS

To a mixture of 150 g of $P_2O_5$ and 300 g of $H_3PO_4$ (85%) is added 40.0 g of di-p-(2-aethoxy-carboxyl)-benzene after which the mixture is stirred for 7 hours at 110° C. The reaction mixture is poured onto ice, the precipitate is filtered off, dried, and dissolved in chloroform. The solution is washed successively with a sodium carbonate solution (20%), 2 N sodium hydroxide solution, and water. The chloroform phase is dried and evaporated to dryness and the residue recrystallised from dioxan yielding 2,3,6,7-tetrahydro-benzo[1,2-b:4,3-b']4H, 4H-dipyrano-4,5-dione (yellow crystals) with melting point: 235° C.

The resulting mother-liquor is evaporated and the [1,2-b:4,5-b] isomer isolated by column chromatography (Silicagel; Benzene/Acetone 98:2).

Melting point: 252° C.

EXAMPLE I

A mixture of 5.0 g of 2,3,6,7-tetrahydro-benzo [1,2-b:4,3-b']4H,4H'-dipyrano-4,5-dione and 20.0 g of hydrazine hydrate is stirred for 2 hours at 20° C. The mixture is poured onto ice, the precipitate is filtered off and crystallised from dioxan yielding 2,3,6,7-tetrahydro-dipyrano[4,3,2-de:2',3',4'-ij]-phthalazine (yield: 97%; melting point: 249° C.

EXAMPLE II

A mixture of 1.2 g of 2,3,6,7-tetrahydro-dipyrano-[4,3,2-de;2',3',4'-ij]phthalazine, 6.0 g of $PCl_5$ and 40 ml of benzene is refluxed during 4 hours. The solvent is evaporated in vacuo and the residue poured into water. The aqueous mixture is heated to boiling temperature, filtered off and the residue crystallised from n-butanol yielding 2,7-dihydro-3,6-tetrachloro-dipyrano[4,3,2-de:2,3,4-ij]-phthalazine. Melting point: 232° C; yield: 77%.

EXAMPLE III

To a solution of 0.07 g of sodium in 5.0 g of methanol (absolute), 0.50 g of 2,7-dihydro-3,6-tetrachlorodipyrano[4,3,2-de:2',3',4'-ij]-phthalazine are added. The mixture is stirred for 30 minutes at 20° C and poured onto ice. The precipitate formed is filtered off and crystallised from ethanol yielding 2,7-dihydro-3,6-dichloro-3,6-dimethoxy-dipyrano[4,3,2-de:2',3',-4'-ij]-phthalazine. Melting point: 181° C (dec.).

In an analogous manner the tetrachloro-compound is converted into the corresponding 2,6-dichloro-3,6-diethoxy,- and 2,6-dichloro-3,6-diisopropoxy-compounds.

EXAMPLE IV

To a solution of 0.01 mol of 2,3,6,7-tetrahydrodipyrano-[4,3,2-de:2',3',4'-ij]-phthalazine in 50 ml of chloroform is added dropwise during 2 hours and at 45° C a solution of 2.5 g of bromine in 15 ml of chloroform. The solvent is then removed in vacuo and the residue is crystallised from ethanol yielding 2,7-dihydro-3,6-tetrabromo-dipyrano-[4,3,2-de:2',3',4'-ij]-phthalazine. Melting point: 216° C.

EXAMPLE V

In accordance with the method as described in Example III the 3,6-tetrabromo-compound according to Example IV is converted into the corresponding 3,6-dibromo-3,6-dimethoxy-, and 3,6-dibromo-3,6-di-n-butoxy-compounds.

EXAMPLE VI

A mixture of 0.20 g of 2,3,6,7-tetrahydro-dipyrano-[4,3,2-de:2',3',4'-ij]-phthalazine and 5.0 g of benzaldehyde is heated up to 130° C. Then 6 drops of concentrated hydrochloric acid are added and the mixture is stirred for 30 minutes at 130° C, after which the mixture is evaporated to dryness in vacuo. The residue is crystallised from n-butanol yielding 3,6-di-benzylidene-2,7-dihydrodipyrano-[4,3,2-de:2',3',4'-ij]-phthalazine in a yield of 88%. Melting point: 242° C.

EXAMPLE VII

To a solution of 8.0 g of 2,3,6,7-tetrahydrodipyrano-[4,3,2-de:2',3',4'-ij]-phthalazine in 50 g of tetrahydrofuran are added, at low temperature, 2.0 g of lithium aluminium hydride. The mixture is stirred for 1 hour at 20° C and then cooled down to 0° C and decomposed by the addition of ice-water. The mixture is filtered and the solution is evaporated to dryness in vacuo. The residue is crystallised from water, after treatment with activated coal, yielding 2,3,4',4,6,7-hexahydro-dipyrano-[4,3,2-de:2',3',4'-ij]-phthalazine. Melting point: 160° C.

| Composition | |
|---|---|
| 2,3,6,7-tetrahydro-dipyrano-[4,3,2-de:2',3',4'-ij]- phthalazine | 50 mg |
| polyvinyl pyrrolidone | 1 mg |
| maize starch | 10 mg |
| magnesium stearate | 5 mg |
| milk sugar | 34 mg |

The powdered active ingredient is blended with maize starch, magnesium stearate and polyvinyl pyrrolidone (PVP) after which the mixture is sieved through a 0.315 mm sieve. Milk sugar is granulated in the usual manner with isopropyl alcohol. The granules obtained are then blended with the above mixture of active ingredient, magnesium stearate and PVP, after which the mass thus obtained is compressed to tablets of about 100 mg.

EXAMPLE II

Coated tablets

The tablets obtained in the previous example are coated in the usual manner with sugar.

EXAMPLE III

Suppositories

| Composition | |
|---|---|
| Active component of Example I | 50 mg |
| Mass for suppositories | 1950 mg |

The active ingredient (particles of 10-50 μ) is dispersed into a molten mass for suppositories at 50° C after which the mass is moulded to 2 g suppositories.

EXAMPLE IV

Capsules

| Composition | |
|---|---|
| 2,3,4,4',6,7-hexahydro-dipyrano-[4,3,2-de-2',3',4'-ij]- phthalazine | 50 mg |
| milk sugar (74 μ) | 50 mg |
| D-(+)-lactose | 25 mg |

The powdered active compound is blended with milk sugar, and D-(+)-lactose intensively, after which the mixture is processed into hard-gel capsules.

EXAMPLE V

Injection preparation

| Composition | |
|---|---|
| 2,3,4,4',6,7-hexahydro-dipyrano-[4,3,2-de:2',3',4'-ij]- | |
| phthalazine hydrochloride | 50 mg |
| water for injection | 4.0 ml |

The active compound is dissolved in water for injection and then made isotonic with sodiumchloride. The solution is sterilised by membrane filtration or heat-treatment at 110° C.

We claim:
1. A hydrodipyrano-phthalazine compound of the formula:

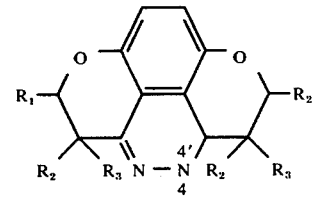

wherein
$R_1$ = hydrogen or lower alkyl,
$R_2$ = hydrogen, chlorine or bromine,
$R_3$ = hydrogen, chlorine, bromine, an alkoxy or aralkyl group, with the proviso that:
$R_3$ = hydrogen or aralkyl if $R_2$ = hydrogen,
$R_3$ = bromine or alkoxy if $R_2$ = bromine,
$R_3$ = chlorine or alkoxy if $R_2$ = chlorine, or
$R_2$ and $R_3$ form together the substituent

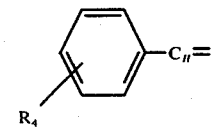

wherein
$R_4$ = hydrogen, halogen, trifluoromethyl, alkyl, alkoxyl, alkylenedioxy, a possibly substituted amino group, or a nitro group.
the 4,4'-bond is saturated or unsaturated, and acid-addition salts of these compounds.

2. A hydrodipyrano-phthalazine compound according to claim 1 having the formula:

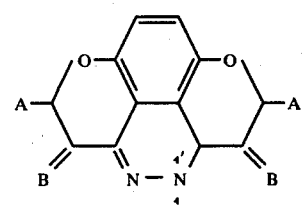

wherein
A = H or methyl,
B = $H_2$, $Cl_2$, $Br_2$, Cl(OCH$_3$), Br(OCH$_3$), H(benzyl) or benzylidene,
the 4,4'-bond is saturated or unsaturated, and acid addition salts of such compounds.

* * * * *